United States Patent [19]

Wiele et al.

[11] 3,965,131

[45] June 22, 1976

[54] PROCESS FOR THE PURIFICATION OF CRUDE CHENODEOXYCHOLIC ACID

[75] Inventors: Dietrich Wiele; Jürgen Riemann, both of Berlin, Germany

[73] Assignee: Schering Aktiengesellschaft, Berlin, Germany

[22] Filed: Jan. 23, 1975

[21] Appl. No.: 543,626

[30] Foreign Application Priority Data

Jan. 25, 1974 Germany............................ 2404102

[52] U.S. Cl. ............................................. 260/397.1
[51] Int. Cl.² ............................................ C07J 9/00
[58] Field of Search ................................ 260/397.2

[56] References Cited
UNITED STATES PATENTS

| | | | |
|---|---|---|---|
| 2,905,677 | 9/1959 | Fevig et al. ................... | 260/397.25 |
| 3,833,620 | 9/1974 | Saltzman........................ | 260/397.1 |
| 3,836,550 | 9/1974 | Jones et al. ................... | 260/397.1 |

*Primary Examiner*—Elbert L. Roberts
*Attorney, Agent, or Firm*—Millen, Raptes & White

[57] ABSTRACT

Crude chenodeoxycholic acid is purified by subjecting an aqueous solution of an alkali salt thereof to continuous liquid-liquid extraction with a water-immiscible organic solvent until substantially all extractable impurities have been extracted. Crystalline pure free acid is obtained therefrom by acidification of the aqueous solution, extracting the free acid with organic solvent and thereafter removing the solvent, the last portion thereof preferably in the presence of water.

8 Claims, No Drawings

PROCESS FOR THE PURIFICATION OF CRUDE CHENODEOXYCHOLIC ACID

BACKGROUND OF THE INVENTION

This invention relates to a process for the purification of crude chenodeoxycholic acid.

Chenodeoxycholic acid is useful in human medicine for the treatment of cholelithiasis, due to its gallstone-dissolving activity.

Chenodeoxycholic acid is generally produced from a natural starting material by esterifying the cholic acid in the cholic acid fraction of bile. The 3- and 7-hydroxy groups are selectively acetylated and the free 12-hydroxy groups is thereafter oxidized to a keto group with chromic acid. The 12-keto compound is then heated in the presence of hydrazine hydrate and potassium hydroxide in ethylene glycol over a prolonged period of time to temperatures of around 200°C.

The crude chenodeoxycholic acid contains, due to its method manufacture, a number of by-products which can be separated only with great difficulties. Also, the thus-obtained product has a rather glass-like property and can by crystallized only with great difficulties. Reprecipitation or recrystallization of the crude chenodeoxycholic acid in a suitable solvent has practically no purifying effect at all.

It is known from German Unexamined Laid-Open Application DOS No. 2,302,774 that purification is possible by treating a methanolic solution of the crude chenodeoxycholic acid with a calcium salt or a strontium salt and then rendering the product alkaline, thus precipitating the calcium or strontium salt of chenodeoxycholic acid. After separation, the product is then acidified, and the purified chenodeoxycholic acid is extracted. The purity of the thus-obtained chenodeoxycholic acid is established by chromatography. The melting point which is a criterion of purity is not mentioned.

For the treatment of cholelithiasis, however, chenodeoxycholic acid of very high purity is required. Impurities can lead to undesired side effects, especially since chenodeoxycholic acid, according to previous experience, must be administered in relatively large dosages and over a rather long period of time.

It is an object of the present invention to provide a method for the purification of crude chenodeoxycholic acid wherein a crystalline chenodeoxycholic acid of both high purity and with a high melting point is obtained.

SUMMARY OF THE INVENTION

According to this invention, chenodeoxycholic acid of high purity is obtained by "perforation" a solution of an alkaline salt of crude chenodeoxycholic acid, i.e., subjecting an aqueous solution of an alkali salt of crude chenodeoxycholic acid to continuous liquid-liquid extraction with a water immiscible organic solvent until substantially all extractable impurities have been extracted. Pure crystalline chenodeoxycholic acid can be isolated from the extracted aqueous solution by acidification with acid, dissolving the precipitated chenodeoxycholic acid in organic solvent and reprecipitating it therefrom in the presence of water.

DETAILED DISCUSSION

The purification process of this invention can conveniently be conducted by first suspending crude chenodeoxycholic acid in water and then rendering the suspension alkaline with an alkali hydroxide, e.g., sodium or potassium hydroxide. It is sometimes advantageous to warm the alkaline suspension somewhat above room temperature to accelerate the dissolution step.

Although the crude chenodeoxycholic acid is preferably purified as its sodium or potassium salt, any soluble salt thereof from which the free acid can be regenerated with strong acid, e.g., dilute hydrochloric or sulfuric acid, can be employed.

The aqueous solution of the salt of the crude chenodeoxycholic acid is then "perforiert" in a "perforator", i.e., subjected to continuous liquid-liquid extraction in a continuous liquid-liquid extraction apparatus, employing a suitable organic solvent or solvent mixture for the impurities, e.g., ethyl acetate, a mixture of isobutanol and toluene or other water-immiscible solvent or mixture of solvents in which the impurities are measurably soluble.

Suitable water-immiscible extractants are, for example, alkanols, e.g., isobutanol, and mixtures thereof with hydrocarbons, e.g., isobutanol/toluene (45:55% by weight), isobutanol/cyclohexane (14:86% by weight) and n-butanol/cyclohexane (10:90% by weight), butan-2-one and higher ketones, ethyl acetate and other simple esters of alkanoic acids and mixtures thereof with hydrocarbons, e.g., ethyl acetate/cyclohexane (54:46% by weight), triethylamine and other amines and diisopropyl ether. A preferred solvent is ethyl acetate.

The continuous liquid-liquid extraction ("perforation") can be effected at temperatures from about room temperature to the boiling point of the solvent or solvent mixture. The optimum extraction conditions, such as selected extractant and volume thereof, selected alkali salt, extraction temperature and time, which are optimum for removal of the impurities and which remove a minimum of the chenodeoxycholic acid along with the impurities can readily be determined by those skilled in the art.

The progress of the extraction can be followed by thin-layer chromatography, i.e., by withdrawal of samples of the dissolved chenodeoxycholic acid salt until it is apparent that continued extraction will no longer result in further quality improvement.

The extraction is preferably conducted at a rate such that the solution of chenodeoxycholic acid is extracted with about 0.05 to 10, preferably about 0.1 to 2, volumes of extracting solvent per hour, calculated on the solution of crude chenodeoxycholic acid. Stirring or other means for dispersing the extracting solvent throughout the chenodeoxycholic acid solution will accelerate the rate at which the acid is purified. The extraction can generally be terminated after 12–24 hours.

The aqueous alkali salt solution of the thus-purified chenodeoxycholic acid is separated from the extracting solvent and then acidified, e.g., with dilute hydrochloric or sulfuric acid, and the pure chenodeoxycholic acid is extracted with an organic solvent which is immiscible with water and in which chenodeoxycholic acid is soluble, for example, ethyl acetate.

Crystalline pure alkaline salt of chenodeoxycholic acid is isolated from the extracting solvent by removal of the solvent, e.g., by evaporation or distillation, preferably at ambient pressure in the case of solvents boiling below 100° C. and under reduced pressure with higher boiling solvents. To ensure the production of chenodeoxycholic acid, at least the last portion of the solvent preferably is removed in the presence of water. Removal of the last traces of solvent in the presence of water promotes the precipitation of the chenodeoxycholic acid in its crystalline form.

The pure chenodeoxycholic acid, thus obtained in crystalline form, is suitably ground in the wet state and is dried under heating for a longer period of time to remove any remaining traces of extractant. The removal of residual solvent is promoted by the use of circulating air and heating at temperatures above room temperature.

Without further elaboration, it is believed that one skilled in the art can, using the preceding description, utilize the present invention to its fullest extent. The following preferred specific embodiments are, therefore, to be construed as merely illustrative and not limitation of the remainder of the disclosure in any way whatsoever.

EXAMPLE 1

393 g. of crude chenodeoxycholic acid is suspended in 830 ml. of water and brought to pH 10.5 ± 0.5 with about 500 ml. of 2N potassium hydroxide, while heating the solution to about 50° C. The solution is continuously extracted in a liquid-liquid continuous extractor (perforator) at 40°–50° C. with ethyl acetate, maintaining a feed of extractant of about 1 liter per liter of solution per hour.

After 10 hours, a sample of the alkaline solution is examined every two hours by thin-layer chromatography. For this purpose, the sample (about 5 ml.) is evaporated in a vacuum forced circulation evaporator and briefly dried at 80° C. Then, 5 $\mu$l. (=250 $\mu$g.) of a 5% mmethanolic solution thereof is applied to silica gel plates, using as the eluent a mixture of chloroform, methanol and glacial acetic acid (85:5:10). The starting material and a methanolic of pure chenodeoxycholic acid are employed as comparison samples. After drying at 100° C., the plate is developed with "Usui" reagent (J. Biochem. 54 [1963] 283).

After the liquid-liquid extraction (perforation) has been completed, the salt solution is filtered over kieselguhr, and 4 l. of ethyl acetate is added thereto. Under agitation, 275 ml. of a 4N hydrochloric acid is added dropwise to acifify the extracted solution. The mixture is stirred for another 15 minutes to ensure dissolution of the chenodeoxycholic acid. The ethyl acetate phase is separated, washed twice with one-liter portions of water, agitated with 30 g. of active carbon at room temperature, and filtered. The filtrate is concentrated until an oil-thickly fluid solution is obtained. The composition, cooled to room temperature, is covered with a layer of 5 l. of water and gradually heated under reduced pressure to 60° C. during this step, first ethyl acetate passes over, followed by water. Crystalline chenodeoxycholic acid precipitates. The thus-obtained crystalline chenodeoxycholic acid is ground in the wet state with twice the volume of water, filtered and dried under air circulation at 80° C. Yield: 295 g. of pure chenodeoxycholic acid, melting at 143°–146° C. and containing less than 0.01% of ethyl acetate.

EXAMPLE 2

25 g. of crude chenodeoxycholic acid is suspended in 150 ml. of water and dissolved with about 64 ml. of 1N sodium hydroxide solution to a pH of 10.5 ± 0.5.

The solution is continuously extracted at 20°–30° C. in a liquid-liquid continuous extraction apparatus (perforator) with a mixture of isobutanol/toluene (45:55% by weight) which is distilled azeotropically.

After the reaction mixture has been purified analogously to Example 1, the separated aqueous salt solution of chenodeoxycholic acid is extracted at least twice with 200 ml. portions of ethyl acetate and then filtered over kieselguhr-carbon. The filtrate is combined with 250 ml. of ethyl acetate, and 55 ml. of 4N hydrochloric acid is added dropwise thereto. The mixture is further worked up as described in Example 1, yielding 18 g. of pure chenodeoxycholic acid, m.p. 143.0°–145.5° C. having a solvent content, as determined by gas chromatography, of <0.01%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the purification of crude chenodeoxycholic acid which comprises subjecting an aqueous solution of an alkali salt of crude chenodeoxycholic acid to exhaustive continuous liquid-liquid extraction with an immiscible organic solvent, separating the thus-purified aqueous solution and then acidifying the separated solution to precipitate the chenodeoxycholic acid therefrom.

2. A process according to claim 1 wherein the crude chenodeoxycholic acid is purified as its sodium or potassium salt.

3. A process according to claim 1 wherein the extracting solvent is ethyl acetate or a mixture of isobutanol and toluene.

4. A process according to claim 1 wherein the precipitated pure chenodeoxycholic acid is dissolved in an organic solvent and the solvent then removed in the presence of water to precipitate crystalline pure chenodeoxycholic acid therefrom.

5. A process according to claim 4 wherein the crude chenodeoxycholic acid is purified as its sodium or potassium salt and wherein the extracting solvent is ethyl acetate or a mixture is isobutanol and toluene.

6. A process according to claim 5 wherein the precipitated pure chenodeoxycholic acid is dissolved in ethyl acetate, which is thereafter removed by heating the solution in the presence of water.

7. A process according to claim 1 wherein the extracting solvent is ethyl acetate.

8. A process according to claim 3 wherein the aqueous solution is acidified with dilute hydrochloric or sulfuric acid.

* * * * *